United States Patent [19]

Berg

[11] Patent Number: 5,633,402
[45] Date of Patent: May 27, 1997

[54] SEPARATION OF FORMIC ACID FROM ACETIC ACID BY AZEOTROPIC DISTILLATION

[75] Inventor: Lloyd Berg, 1314 S. Third Ave., Bozeman, Mont. 59715

[73] Assignee: Lloyd Berg

[21] Appl. No.: 522,546

[22] Filed: Sep. 1, 1995

[51] Int. Cl.$^6$ .................................................. C07C 51/42
[52] U.S. Cl. ........................ 562/608; 562/607; 562/609
[58] Field of Search .................................. 562/608, 607, 562/609

[56] References Cited

U.S. PATENT DOCUMENTS

| | | | |
|---|---|---|---|
| 2,170,834 | 8/1939 | Othmer | 202/42 |
| 2,425,542 | 8/1947 | Krieble et al. | 260/541 |
| 4,268,362 | 5/1981 | Ogawa et al. | 203/28 |
| 5,160,412 | 11/1992 | Berg | 203/16 |

*Primary Examiner*—Joseph Conrad
*Assistant Examiner*—Rosalynd Williams

[57] ABSTRACT

Formic acid is difficult to separate from acetic acid by conventional distillation or rectification because of the proximity of their boiling points. Formic acid can be readily separated from acetic acid by using azeotropic distillation. Effective agents are acetonitrile and isopropyl acetate.

2 Claims, No Drawings

SEPARATION OF FORMIC ACID FROM ACETIC ACID BY AZEOTROPIC DISTILLATION

FIELD OF THE INVENTION

This invention relates to a method for separating formic acid from acetic acid using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

Formic acid has been separated from acetic acid commercially using benzene as the azeotrope forming agent but because of the hazardous characteristics of benzene, its use has been largely abandoned. Carbon tetrachloride and cyclohexane have been reported but are not as effective as benzene as an azeotrope former.

Berg & Wytcherley, U.S. Pat. No. 5,264,086 used cyclopentane as the azeotrope former. Its relative volatility in this separation is 1.44, about the same as benzene.

Formic acid, B.P. 101° C. and acetic acid, B.P. 118° C. have a relative volatility of 1.23 and are difficult to separate by conventional rectification. Table 1 shows that to get 99% purity, sixty actual plates are required. For an agent giving a relative volatility of 2.0, 17 actual plates are required and with a relative volatility of 3.0, only 12 actual plates are required. An improvement of this magnitude represents a clear economic and operational advantage to the separation of these industrially important chemicals.

TABLE 1

Theoretical and Actual Plates Required vs. Relative Volatility for Formic Acid - Acetic Acid Separation

| Relative Volatility | Theoretical Plates Required At Total Reflux, 99% Purity | Actual Plates Required, 75% Eff. |
| --- | --- | --- |
| 1.23 | 45 | 60 |
| 1.34 | 32 | 43 |
| 1.44 | 25 | 33 |
| 2.0 | 13 | 17 |
| 3.0 | 9 | 12 |

OBJECTIVE OF THE INVENTION

The object of this invention is to provide a process or method of azeotropic distillation that will enhance the relative volatility of formic acid to acetic acid in their separation in a rectification column. It is a further object of this invention to identify certain organic compounds that are stable, are effective as azeotropic distillation agents and can be readily separated from formic acid or acetic acid and recycled to the azeotropic distillation column with little decomposition.

SUMMARY OF THE INVENTION

The objects of this invention are provided by a process for the separation of formic acid from acetic acid which entails the use of certain organic compounds when separately employed as the agent in azeotropic distillation.

TABLE 2

Effective Azeotropic Distillation Agents For Separting Formic Acid From Acetic Acid

| Compounds | Relative Volatility |
| --- | --- |
| None | 1.23 |
| Methyl acetate | 1.35 |
| Isopropyl ether | 1.8 |
| Methyl t-butyl ether | 1.7 |
| Acetal | 1.3 |
| Tetrahydrofuran | 1.65 |
| 2,2-Dimethoxypropane * | 3.3 |
| Acetonitrile * | 2.3 |
| Nitromethane | 2.1 |
| Acetaldehyde oxime | 2.3 |
| Isopropyl acetate | 2.5 |
| Benzene | 1.45 |
| Propyl formate | 1.75 |
| Methyl formate * | 3.2 |
| 2,3-Butanediol | 3.5 |

* Brings formic acid out as overhead product

DETAILED DESCRIPTION OF THE INVENTION

I have discovered that certain organic compounds will effectively increase the relative volatility between formic acid and acetic acid during rectification when employed as the agent in azeotropic distillation. Table 2 summarizes the data obtained with these agents. The agents which are effective are methyl acetate, isopropyl ether, isopropyl acetate, methyl t-butyl ether, acetal, tetrahydrofuran, 2,2-dimethoxypropane, acetonitrile, nitromethane, acetaldehyde oxime, propyl formate, methyl formate and 2,3-butanediol.

THE USEFULNESS OF THE INVENTION

The usefulness or utility of this invention can be demonstrated by referring to the data presented in Tables 1 and 2. All of the successful agents show that formic acid can be separated from acetic acid by means of azeotropic distillation in a rectification column and that the ease of separation as measured by relative volatility is considerable.

WORKING EXAMPLES

Example 1

Twenty grams of formic acid, 80 grams of acetic acid and 50 grams of acetonitrile were charged to a vapor-liquid equilibrium still and refluxed for six hours. The vapor composition was 21.5% formic acid, 78.5% acetic acid; the liquid composition was 10.4% formic acid, 89.6% acetic acid which is a relative volatility of formic acid to acetic acid of 2.3.

Example 2

Seventy-five grams of formic acid, 75 grams of acetic acid and 100 grams of isopropyl acetate were charged to a glass perforated plate rectification column containing 7.3 theoretical plates. After three hours at total reflux, overhead and bottoms samples were taken and analysed. The overhead was 1.5% formic acid, 98.5% acetic acid; the bottoms was 92.6% formic acid, 7.4% acetic acid which is a relative volatility of acetic acid to formic acid of 2.5.

I claim:

1. A method for recovering formic acid from a mixture of formic acid and acetic acid which comprises distilling a mixture of formic acid and acetic acid in the presence of an azeotrope forming agent, recovering the formic acid and the azeotrope forming agent as overhead product and obtaining the acetic acid from the stillpot, wherein said azeotrope forming agent is one material selected from the group consisting or 2,2-dimethoxypropane and methyl formate.

2. A method for recovering acetic acid from a mixture of acetic acid and formic acid which comprises distilling a mixture of acetic acid and formic acid in the presence of an azeotrope forming agent, recovering the acetic acid and the azeotrope forming agent as overhead product and obtaining the formic acid from the stillpot, wherein said azeotrope forming agent is one material selected from the group consisting of methyl-t-butyl ether, acetal, tetrahydrofuran, nitromethane, acetaldehyde oxime, propyl formate and 2,3-butanediol.

* * * * *